United States Patent
Grinberg

(10) Patent No.: US 7,341,591 B2
(45) Date of Patent: Mar. 11, 2008

(54) ANTERIOR BUTTRESS STAPLE

(75) Inventor: Alexander D. Grinberg, Newton, MA (US)

(73) Assignee: DePuy Spine, Inc., Raynham, MA (US)

( * ) Notice: Subject to any disclaimer, the term of this patent is extended or adjusted under 35 U.S.C. 154(b) by 736 days.

(21) Appl. No.: 10/354,441

(22) Filed: Jan. 30, 2003

(65) Prior Publication Data

US 2004/0153078 A1     Aug. 5, 2004

(51) Int. Cl.
*A61B 17/56* (2006.01)
*A61F 2/30* (2006.01)

(52) U.S. Cl. ....................................... 606/75
(58) Field of Classification Search ................. 606/74, 606/75, 69, 219, 70, 71, 220, 221
See application file for complete search history.

(56) References Cited

U.S. PATENT DOCUMENTS

| | | | |
|---|---|---|---|
| 3,604,414 A | | 9/1971 | Borges |
| 3,741,205 A | * | 6/1973 | Markolf et al. ............... 606/61 |
| 4,029,091 A | * | 6/1977 | von Bezold et al. .......... 606/69 |
| 4,388,921 A | | 6/1983 | Sutter |
| 4,484,570 A | | 11/1984 | Sutter |
| 4,509,890 A | | 4/1985 | Hill |
| 4,611,580 A | | 9/1986 | Wu |
| 4,621,961 A | | 11/1986 | Gulistan |
| 4,743,260 A | | 5/1988 | Burton |
| 4,763,644 A | | 8/1988 | Webb |
| 4,790,297 A | | 12/1988 | Luque |
| 4,793,335 A | * | 12/1988 | Frey et al. .................... 606/73 |
| 4,805,602 A | | 2/1989 | Puno et al. |
| 4,887,596 A | | 12/1989 | Sherman |
| 4,913,134 A | | 4/1990 | Luque |
| 4,946,458 A | | 8/1990 | Harms et al. |
| 4,950,269 A | | 8/1990 | Gaines, Jr. |
| 5,005,562 A | | 4/1991 | Cotrel |
| 5,108,395 A | | 4/1992 | Laurain |
| 5,129,388 A | | 7/1992 | Vignaud et al. |
| 5,147,361 A | | 9/1992 | Ojima et al. |

(Continued)

FOREIGN PATENT DOCUMENTS

DE             3722590         7/1987

(Continued)

OTHER PUBLICATIONS

Product Brochure "PEAK Polyaxial Cervical Plating System" DePuy Acromed, Inc., 1999.

(Continued)

*Primary Examiner*—Anuradha Ramana
(74) *Attorney, Agent, or Firm*—Nutter, McClennen & Fish LLP

(57) ABSTRACT

An anterior buttress staple and screw system is provided that can be used to hold an implant such as a disc prosthesis in place and thereby prevent its migration out of the spinal column. The buttress staple comprises a screw locking plate having a screw locking design that prevents the screw from backing up and away from the plate. The screw is configured to provide an interference fit with the screw locking plate, and can be used as a staple removal tool during revision surgery when the screw locking plate needs to be lifted from the bone surface on which it is attached.

27 Claims, 3 Drawing Sheets

U.S. PATENT DOCUMENTS

| | | |
|---|---|---|
| 5,154,719 A | 10/1992 | Cotrel |
| 5,180,381 A | 1/1993 | Aust |
| 5,217,497 A | 6/1993 | Mehdian |
| 5,246,443 A | 9/1993 | Mai |
| 5,261,910 A | 11/1993 | Warden et al. |
| 5,261,912 A | 11/1993 | Frigg |
| 5,261,913 A | 11/1993 | Marnay |
| 5,314,427 A * | 5/1994 | Goble et al. .................... 606/72 |
| 5,324,290 A | 6/1994 | Zdeblick et al. |
| 5,334,203 A | 8/1994 | Wagner |
| 5,360,431 A | 11/1994 | Puno et al. |
| 5,364,399 A | 11/1994 | Lowery et al. |
| 5,381,588 A | 1/1995 | Nelson |
| 5,385,583 A | 1/1995 | Cotrel |
| 5,395,372 A | 3/1995 | Holt et al. |
| 5,403,315 A | 4/1995 | Ashman |
| 5,423,826 A | 6/1995 | Coates et al. |
| 5,437,669 A | 8/1995 | Yuan et al. |
| 5,474,555 A | 12/1995 | Puno et al. |
| 5,476,464 A | 12/1995 | Metz-Stavenhagen et al. |
| 5,520,689 A | 5/1996 | Schlapfer et al. |
| 5,527,314 A | 6/1996 | Brumfield et al. |
| 5,536,268 A | 7/1996 | Griss |
| 5,549,612 A | 8/1996 | Yapp et al. |
| 5,554,157 A | 9/1996 | Errico et al. |
| 5,578,034 A * | 11/1996 | Estes ............................ 606/61 |
| 5,601,553 A | 2/1997 | Trebing |
| 5,603,713 A | 2/1997 | Aust |
| 5,607,428 A | 3/1997 | Lin |
| 5,616,142 A | 4/1997 | Yuan |
| 5,616,144 A | 4/1997 | Yapp |
| 5,634,926 A | 6/1997 | Jobe |
| 5,662,655 A * | 9/1997 | Laboureau et al. ............ 606/75 |
| 5,669,911 A | 9/1997 | Errico et al. |
| 5,676,666 A | 10/1997 | Oxland |
| 5,681,311 A | 10/1997 | Foley et al. |
| 5,683,390 A | 11/1997 | Metz-Stavenhagen et al. |
| 5,683,393 A | 11/1997 | Ralph |
| 5,690,630 A | 11/1997 | Errico et al. |
| 5,697,929 A | 12/1997 | Mellinger |
| 5,713,898 A | 2/1998 | Stucker et al. |
| 5,716,356 A | 2/1998 | Biedermann et al. |
| 5,733,286 A | 3/1998 | Errico et al. |
| 5,735,853 A | 4/1998 | Olerud |
| 5,738,685 A | 4/1998 | Halm et al. |
| 5,752,957 A | 5/1998 | Ralph et al. |
| 5,772,662 A * | 6/1998 | Chapman et al. ............. 606/69 |
| 5,779,707 A * | 7/1998 | Bertholet et al. ............. 606/75 |
| 5,797,911 A | 8/1998 | Sherman et al. |
| 5,810,823 A * | 9/1998 | Klaue et al. ................... 606/69 |
| 5,851,207 A | 12/1998 | Cesarone |
| 5,863,293 A | 1/1999 | Richelsoph |
| 5,865,847 A | 2/1999 | Kohrs et al. |
| 5,879,350 A | 3/1999 | Sherman et al. |
| 5,882,350 A | 3/1999 | Ralph et al. |
| 5,888,215 A * | 3/1999 | Roos et al. .................... 623/33 |
| 5,899,904 A * | 5/1999 | Errico et al. ................... 606/61 |
| 5,902,303 A | 5/1999 | Eckhof |
| 5,904,683 A | 5/1999 | Pohndorf et al. |
| 5,910,142 A | 6/1999 | Tatar |
| 5,916,200 A * | 6/1999 | Eppley et al. ................ 604/178 |
| 5,931,838 A * | 8/1999 | Vito ............................ 606/61 |
| 5,951,558 A | 9/1999 | Fiz |
| 5,954,722 A | 9/1999 | Bono |
| 5,964,760 A | 10/1999 | Richelsoph |
| 5,989,254 A | 11/1999 | Katz |
| 6,017,345 A | 1/2000 | Richelsoph |
| 6,030,389 A | 2/2000 | Wagner et al. |
| 6,036,693 A | 3/2000 | Yuan et al. |
| 6,059,785 A | 5/2000 | Schavan et al. |
| 6,066,142 A | 5/2000 | Serbousek et al. |
| 6,129,730 A | 10/2000 | Bono et al. |
| 6,139,316 A | 10/2000 | Sachdeva |
| 6,139,550 A | 10/2000 | Michelson |
| 6,152,927 A | 11/2000 | Farris et al. |
| 6,161,263 A | 12/2000 | Anderson |
| 6,193,721 B1 | 2/2001 | Michelson |
| 6,206,882 B1 * | 3/2001 | Cohen ........................ 606/69 |
| D440,311 S | 4/2001 | Michelson |
| 6,224,602 B1 | 5/2001 | Hayes |
| 6,235,028 B1 | 5/2001 | Brumfield |
| 6,235,034 B1 | 5/2001 | Bray, Jr. |
| 6,241,731 B1 | 6/2001 | Fiz |
| 6,258,089 B1 | 7/2001 | Campbell et al. |
| 6,261,291 B1 | 7/2001 | Talaber et al. |
| 6,273,889 B1 | 8/2001 | Richelsoph |
| 6,293,949 B1 | 9/2001 | Justis |
| D449,692 S | 10/2001 | Michelson |
| 6,303,136 B1 | 10/2001 | Li |
| 6,303,139 B1 | 10/2001 | Passi |
| 6,306,136 B1 | 10/2001 | Baccelli |
| 6,331,179 B1 | 12/2001 | Freid |
| 6,336,928 B1 * | 1/2002 | Guerin et al. ................. 606/61 |
| 6,342,055 B1 | 1/2002 | Eisermann et al. |
| 6,342,057 B1 | 1/2002 | Brace et al. |
| 6,355,038 B1 | 3/2002 | Pisharodi |
| 6,379,364 B1 | 4/2002 | Brace et al. |
| 6,413,259 B1 | 7/2002 | Lyons |
| 6,428,542 B1 | 8/2002 | Michelson |
| 6,443,953 B1 | 9/2002 | Perra et al. |
| 6,471,705 B1 | 10/2002 | Biedermann et al. |
| 6,503,250 B2 | 1/2003 | Paul |
| 6,520,963 B1 | 2/2003 | McKinley |
| 6,527,776 B1 | 3/2003 | Michelson |
| 6,533,786 B1 | 3/2003 | Needham |
| 6,558,423 B1 | 5/2003 | Michelson |
| 6,565,571 B1 | 5/2003 | Jackowski |
| 6,575,975 B2 * | 6/2003 | Brace et al. ................... 606/69 |
| 6,595,993 B2 | 7/2003 | Donno |
| 6,602,255 B1 | 8/2003 | Campbell et al. |
| 6,620,167 B2 | 9/2003 | Deslauriers et al. |
| 6,626,907 B2 * | 9/2003 | Campbell et al. ............. 606/61 |
| 6,652,525 B1 * | 11/2003 | Assaker et al. ............... 606/61 |
| 6,669,473 B1 | 12/2003 | Maino et al. |
| 6,669,700 B1 | 12/2003 | Farris |
| 6,692,498 B1 * | 2/2004 | Niiranen et al. .............. 606/69 |
| 6,695,846 B2 | 2/2004 | Richelsoph |
| 6,755,833 B1 | 6/2004 | Paul |
| 6,764,489 B2 | 7/2004 | Ferree |
| 6,843,791 B2 | 1/2005 | Serhan |
| 7,001,389 B1 | 2/2006 | Navarro et al. |
| 7,048,739 B2 * | 5/2006 | Konieczynski et al. ....... 606/73 |
| 7,166,111 B2 | 1/2007 | Kolb |
| 7,175,624 B2 * | 2/2007 | Konieczynski et al. ....... 606/71 |
| 2001/0037112 A1 | 11/2001 | Brace et al. |
| 2001/0041894 A1 | 11/2001 | Campbell et al. |
| 2002/0082606 A1 | 6/2002 | Suddaby |
| 2002/0147450 A1 | 10/2002 | Lehuec |
| 2002/0147453 A1 * | 10/2002 | Gambale ..................... 606/71 |
| 2002/0193795 A1 * | 12/2002 | Gertzbein et al. ............. 606/61 |
| 2003/0040749 A1 | 2/2003 | Grabowski |
| 2003/0060828 A1 | 3/2003 | Michelson |
| 2003/0078583 A1 | 4/2003 | Biedermann et al. |
| 2003/0135213 A1 | 7/2003 | Lehuec |
| 2003/0187440 A1 | 10/2003 | Richelsoph |
| 2003/0187442 A1 * | 10/2003 | Richelsoph et al. .......... 606/70 |
| 2003/0187443 A1 | 10/2003 | Lauryssen et al. |
| 2003/0225409 A1 * | 12/2003 | Freid et al. ................... 606/69 |
| 2003/0233098 A1 | 12/2003 | Markworth |
| 2004/0015169 A1 | 1/2004 | Gause |
| 2004/0015174 A1 | 1/2004 | Null |
| 2004/0019353 A1 | 1/2004 | Fried et al. |
| 2004/0030340 A1 | 2/2004 | Pisharodi |
| 2004/0034352 A1 | 2/2004 | Needham |

| | | |
|---|---|---|
| 2004/0034354 A1 | 2/2004 | Paul |
| 2004/0039383 A1 | 2/2004 | Jackson |
| 2004/0087951 A1 | 5/2004 | Khalili |
| 2004/0092947 A1 | 5/2004 | Foley |
| 2004/0097935 A1 | 5/2004 | Richelsoph |
| 2004/0127899 A1 | 7/2004 | Konieczynski et al. |
| 2004/0127900 A1* | 7/2004 | Konieczynski et al. ....... 606/69 |
| 2004/0127904 A1 | 7/2004 | Konieczynski et al. |
| 2004/0133205 A1 | 7/2004 | Thramann |
| 2005/0049593 A1 | 3/2005 | Duong |
| 2005/0273105 A1 | 12/2005 | Konieczynski et al. |

FOREIGN PATENT DOCUMENTS

| | | |
|---|---|---|
| FR | 87 17852 | 12/1987 |
| GB | 2 173 104 | 10/1986 |
| WO | WO 99/56653 | 11/1999 |
| WO | WO 9956653 * | 11/1999 |
| WO | WO 00/25689 | 5/2000 |
| WO | WO 02/09605 | 2/2002 |
| WO | WO-02/45592 | 6/2002 |
| WO | WO 03/007826 | 1/2003 |
| WO | WO 03/024344 | 3/2003 |

OTHER PUBLICATIONS

Product Brochure "PEAK Anterior Compression Plate" DePuy Acromed, Inc., 1996.
Product Brochure "The Titanium Buttress Locking Plate" Synthes Spine, 1997.
Product Brochure "AcroMed Special Products" DePuy Acromed, Inc., 1998.
Product Brochure "Surgical Technique PROFILE Anterior Thoraco-Lumbar Plating System" DePuy Acromed, Inc., 2002.
Product Brochure "ABC Anterior Cervical Plating System" AESCULAP, 1999.
D. Bynum, Jr. et al., Holding Characteristics of Fasteners in Bone, Experimental Mechanics, TX A&M Univ. p. 363-69 (Aug. 1971).
Product Brochure "Introducing EBI VueLock Anterior Cervical Plate System," EBI, A Biomet Company (2001).
Product Brochure "Introducing the Low Profile ZEPHIR Anterior Cervical Plate System" Medtronic, Sofamor Danek; Apr. 1, 2003.
Web Page www.ebimedicalc.com/products/spine/vuelock.html, "EBI VueLock, Anterior Cervical Plate System" EBI, A Biomet Company; Apr. 1, 2003.
Web Page www.sofamordanek.com, "Zephir Anterior Cervical Plate System," Medtronic Sofamor Danek; Apr. 1, 2003.

* cited by examiner

ANTERIOR BUTTRESS STAPLE

CROSS-REFERENCE TO RELATED APPLICATIONS

Not applicable.

STATEMENT REGARDING FEDERALLY SPONSORED RESEARCH

Not Applicable.

FIELD OF THE INVENTION

The present invention relates to medical implants useful for orthopedic and spinal surgeries. More particularly, this invention relates to a buttress staple and screw system for preventing the migration of implants such as intervertebral disc prostheses after implantation.

BACKGROUND OF THE INVENTION

Injury or damage to bones, discs, joints, and ligaments of the body are often a result of advancing age, trauma, tumor growth, or a disease process. In patients suffering from a degenerative disc disease, the injury often manifests itself as damage or degeneration of a spinal disc, the result of which can range from mild to severe chronic back pain. Intervertebral discs are fibrous cartilage pads that allow the spine to bend and serve as "shock" absorbers for the vertebrae, absorbing pressure delivered to the spinal column. Additionally, they maintain the proper anatomical separation between two adjacent vertebra. This separation is necessary for allowing both the afferent and efferent nerves to exit and enter, respectively, the spinal column.

To alleviate the pain caused by a ruptured or herniated disc, current treatment methods include a discectomy in which the affected intervertebral disc is removed. If desired, a disc prosthesis can be inserted between the vertebrae to fill the space left by the removed disc. Thereafter, the two adjacent vertebral bodies can be fused together in a process commonly referred to as spinal fusion. The disc prosthesis restores the angular relationship between the adjacent vertebrae to be fused, and provides the material for bone growth to occur between the two vertebral bodies.

A variety of these disc implants are known to exist. These artificial intervertebral discs can include fusion cages made from metals and/or synthetic materials. Many prostheses can also be fashioned from allograft bone that is harvested from portions of long bone including the femur, humerus, tibia, fibula, ulna and radius.

The success or failure of the fusion can often depend upon the type and properties of the prosthesis that is placed between the adjacent vertebral bodies. Obviously, the prosthesis must be sufficiently strong to withstand the loads encountered in the spine, it must be biocompatible, and it should permit the ingrowth of bone to complete the fusion. Perhaps more importantly, the prosthesis must have properties and geometries that permit the prosthesis to remain fixed in the desired position. Because of the continuous forces that act upon the vertebrae and especially the disc prosthesis in a dynamic environment like the human spinal column, the tendency of the prosthesis to migrate due to shifting, rotation or slippage poses a constant threat to the success of the bone fusion.

SUMMARY OF THE INVENTION

The present invention provides an anterior buttress staple and screw system that can be used to hold an implant such as a disc prosthesis in place and thereby prevent its migration out of the spinal column. The buttress staple comprises as a screw locking plate having a screw locking design that prevents the screw from backing up and away from the implant it holds. The screw is configured to provide an interference fit with the screw locking plate, and can be used as a staple removal tool during revision surgery when the screw locking plate needs to be lifted from the bone surface on which it is attached.

In one exemplary embodiment of the present invention, the screw locking plate is defined by sidewalls connected by endwalls. The screw locking plate includes a first surface and a second, bone-contacting surface opposed to the first surface. The buttress staple further includes an anchoring post that is configured for insertion into bone. The anchoring post extends from the second, bone-contacting surface of the body. The anchoring post can be tapered, and can include surface features such as sharp edges or barbs for engagement with bone.

The screw locking plate further includes a resilient aperture that extends through the first and second surfaces. The resilient aperture has a predefined shape and size, and is configured to expand and contract to receive a screw. For instance, the resilient aperture can be a circular hole or an oblong slot. The resilient aperture can also be countersunk on the first surface of the body. The resilient aperture opens into a slit extending through the first and second surfaces of the body. The slit terminates in a relief hole. The relief hole can be another aperture that is configured to receive a screw and have the same characteristics as the resilient aperture. The slit allows the resilient aperture to expand and contract, and enables the screw locking plate to deform as needed to receive the screw.

In one aspect of the present invention, the screw locking plate has a substantially bow tie-like shape. That is, the midsection of each of the sidewalls and endwalls extends towards a central region of the body. The plate can also be shaped to conform to the contours of the spinal column. For instance, the plate can be bent with respect to a longitudinal axis thereof, and curved with respect to a transverse axis thereof.

Also provided with the anterior buttress staple is a screw configured to be inserted into bone. The screw is defined by a head region at a proximal end. An elongated body that includes a threaded portion extends from the head region to a distal end of the screw. The head region is configured to be secured within the resilient aperture of the screw locking plate. The head region is defined by a top flange, a contact band, and a groove extending therebetween about the circumference of the head region. The contact band is situated adjacent to the elongated body, and is sized to provide an interference fit with the resilient aperture.

Further features of the invention, its nature and various advantages, will be more apparent from the accompanying drawings and the following detailed description of the drawings and the preferred embodiments.

BRIEF DESCRIPTION OF THE DRAWINGS

The invention can be more fully understood from the following detailed description taken in conjunction with the accompanying drawings, in which.

DETAILED DESCRIPTION OF THE INVENTION

Figure 1A:
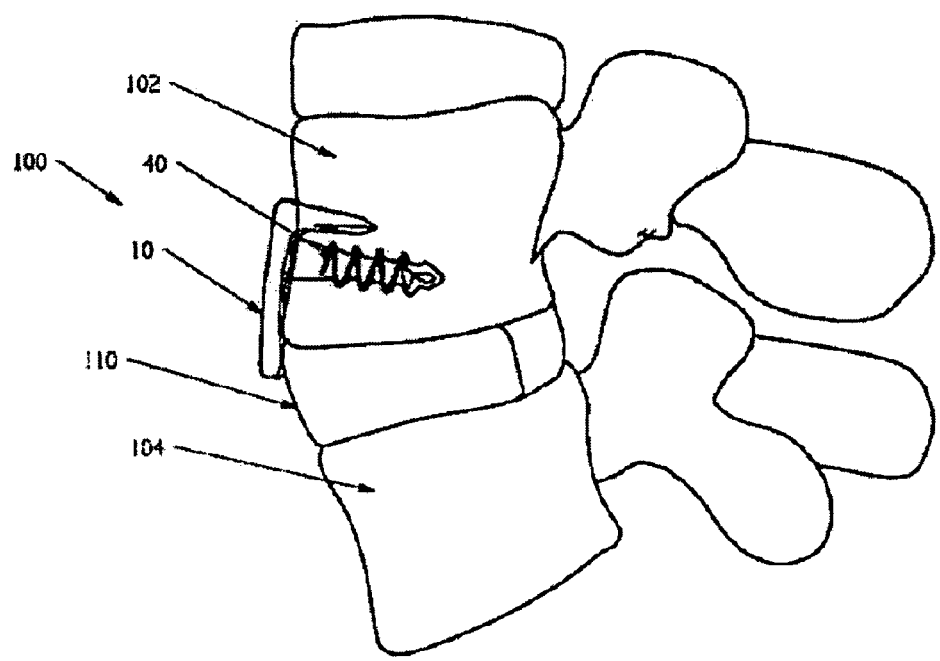
FIG. 1A is a partial cutaway side view of an implanted anterior buttress staple system of the present invention.
Figure 1B:
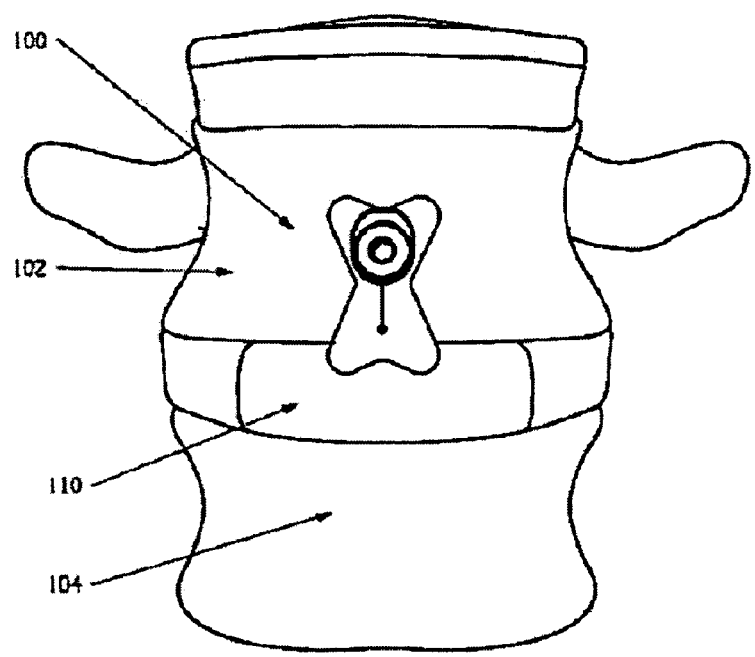
FIG. 1B is a detailed end view a portion of the implanted anterior staple buttress system shown in FIG. 1A.

The present invention provides an anterior buttress staple and screw system 100 that is configured to prevent the migration of an implant, such as a disc prosthesis, within the patient. The buttress staple and screw system 100 comprises two main components: a buttress staple 10 and a screw 40. As illustrated in FIGS. 1A and 1B in which there is shown a fully assembled system 100 used in an anterior lumbar fusion procedure, the buttress staple 10 is anteriorly secured to a vertebral body 102 with the screw 40 to prevent a disc prosthesis 110 from expulsion. When secured to the vertebral body 102 as depicted, the implanted buttress staple 10 acts like a bracket, urging against the disc prosthesis 110 between adjacent vertebral bodies 102, 104 to keep the prosthesis 110 from moving out of position. The buttress staple 10 is configured with a simple and reliable screw locking design that prevents the screw 40 from backing up and out of the staple 10.

Figure 2:
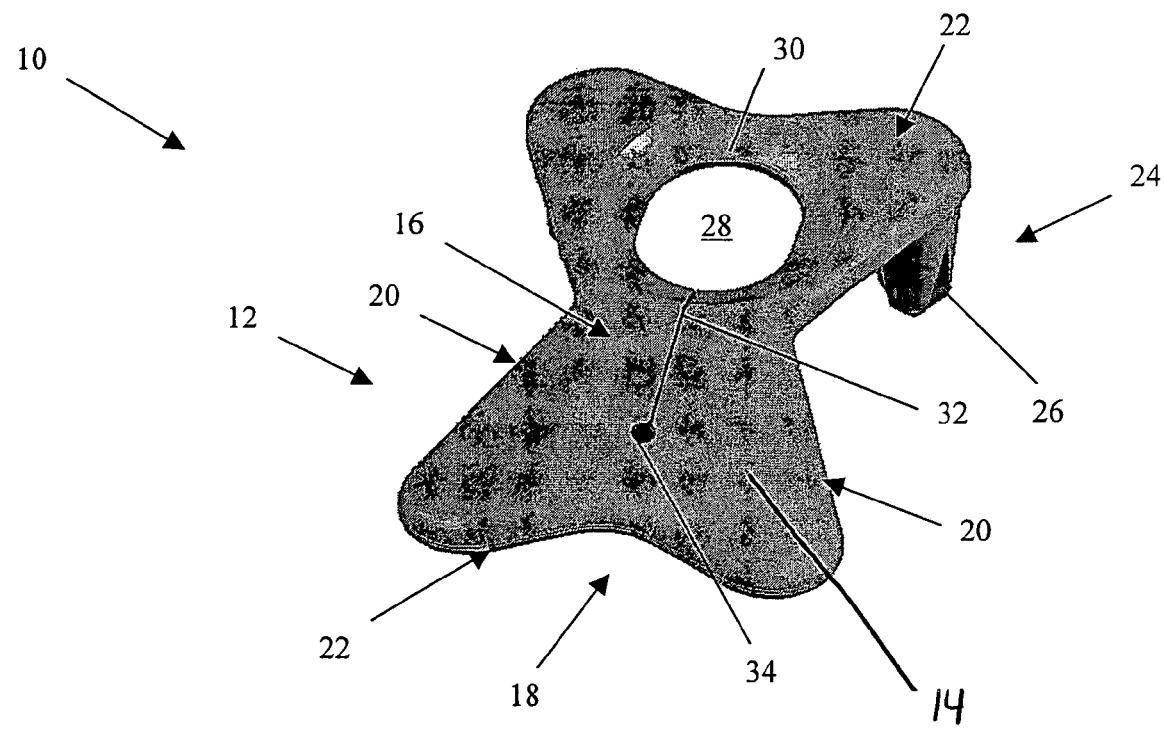
FIG. 2 is a perspective view of a buttress staple of the present invention.

Turning now to the first component of the system 100 and particularly to FIG. 2, an exemplary buttress staple 10 of the present invention is shown. The buttress staple 10 comprises a screw locking plate 12 and an anchoring post 24 for securing the screw locking plate to bony tissue. The screw locking plate 12 includes a first surface 16 and a second, bone-contacting surface 18 opposed to the first surface 16. The plate 12 is defined by sidewalls 20 which are connected by endwalls 22. In an exemplary embodiment of the present invention, the plate 12 has a substantially bow tie-like shape. That is, the midsection of each of the sidewalls 20 and endwalls 22 extends towards a central region of the plate 12 as shown in FIG. 2. The plate 12 can also be shaped to conform to the contours of the spinal column. For instance, as depicted in FIGS. 1A and 1B, the plate 12 can be bent with respect to a longitudinal axis thereof, and curved with respect to a transverse axis thereof. This provides the plate 12 with a curvature in two planes. The curve of the screw locking plate 12 along its longitudinal axis enables it to closely match the curves of the spinal column and provide a better fit once implanted. The curve of the plate 12 along an axis transverse to the longitudinal axis allows it to urge against the disc prosthesis 110 beneath vertebral body 102 and hold the implant in place as shown.

Figure 4A:
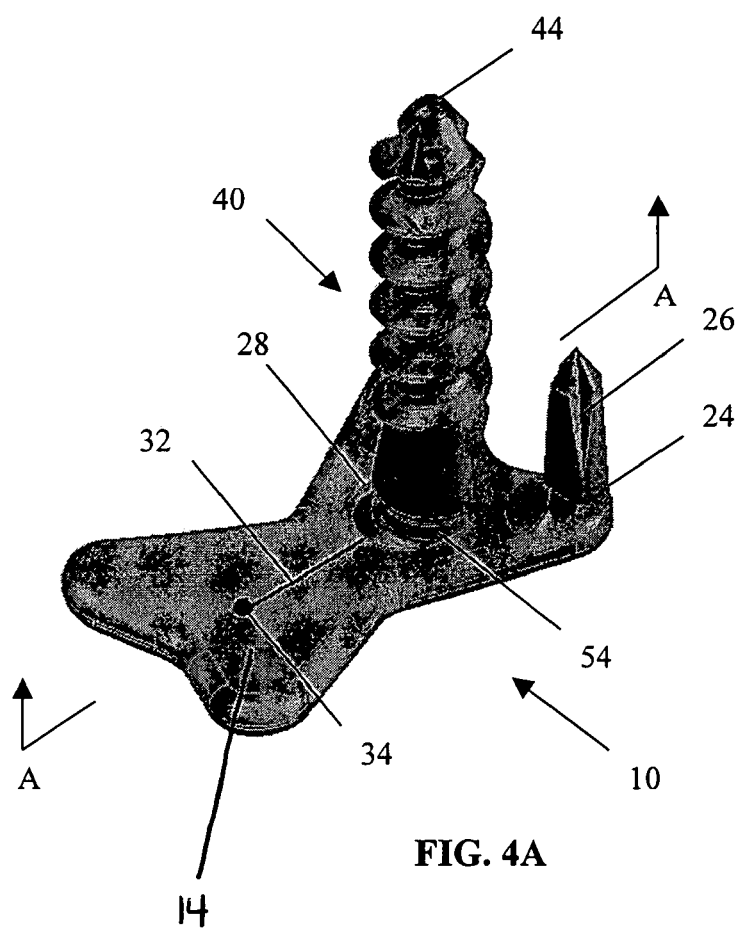
FIG. 4A is a perspective view of the buttress staple of FIG. 2 with the screw of FIG. 3.

The buttress staple 10 further includes an anchoring post 24 that is configured for insertion into bone. The anchoring post 24 extends from the second, bone-contacting surface 18 of the screw locking plate 12. As shown in FIGS. 2 and 4A, the anchoring post 24 can be tapered, and can include surface features such as sharp edges 26 for engagement with bone. Of course, other surface features such as barbs or spikes can also be employed to provide the anchoring post 24 with the ability to penetrate into bone tissue. During assembly, the anchoring post 24 is tapped into the bone to hold the buttress staple 10 in the proper location on the bone segment. As illustrated, two anchoring posts 24 exist near an endwall 22 of the screw locking plate 12. It is understood, however, that several or even a single anchoring post 24 can be employed. The anchoring post 24 or posts can be situated anywhere along the screw locking plate 12 as appropriate, so long as the post 24 or posts do not interfere with the holding function or attachment of the buttress staple 10 to the patient.

The screw locking plate 12 further includes a resilient aperture 28 that extends through the first and second surfaces 16, 18. The resilient aperture 28 has a predefined shape and size, and is configured to expand and contract to receive a screw. For instance, the resilient aperture 28 can be a circular hole or an oblong slot as illustrated in FIG. 2. The resilient aperture 28 can also include a countersink 30 on the first surface 16 of the body 14. The resilient aperture 28 opens into a slit 32 extending through the first and second surfaces 16, 18 of the body 14. The slit 32 terminates into a relief hole 34. The relief hole 34 serves to alleviate the stresses at the terminal end of the slit 32 during plate 12 deformation. However, the relief hole 34 can also serve a more substantial function, and can be formed as another aperture that is configured to receive a screw and have the same characteristics as the resilient aperture 28. That is, it is contemplated that the slit 32 can extend between two resilient apertures 28 that are configured to receive a bone screw, and that the body 14 can include more than one slit 32 having apertures 28, 34 connected thereto. Such a configuration would provide a greater ability to secure the screw locking plate 10 to the bone segment.

Figure 3:
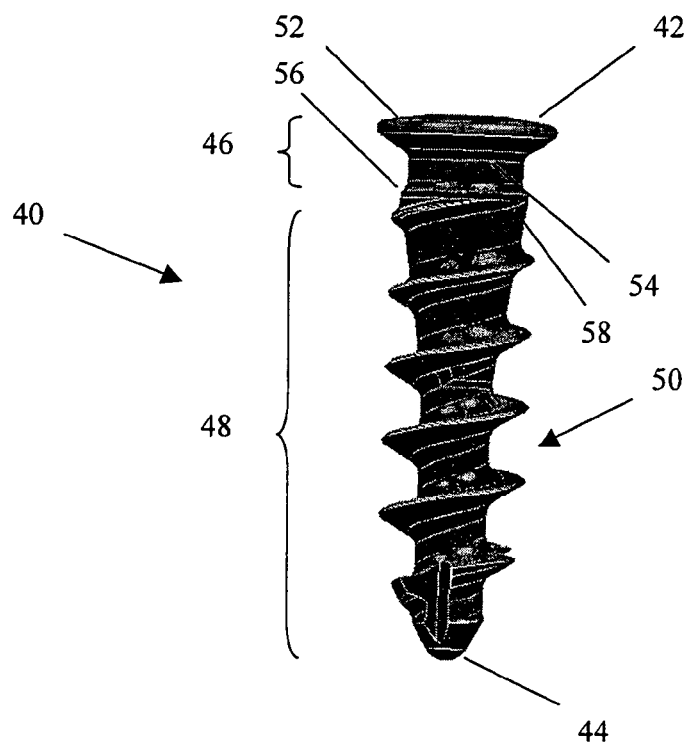
FIG. 3 is a side view of a screw of the present invention.

Also provided with the present system is a screw 40 configured to be inserted into bone. As illustrated in FIG. 3, the screw 40 is defined by a head region 46 at a proximal end 42. An elongated body 48 that includes a threaded portion 50 extends from the head region 46 to a distal end 44 of the screw 40. The head region 46 is defined by a top flange 52, a contact band 56, and a groove 54 extending therebetween about the circumference of the head region 46. The contact band 56 is situated adjacent to the elongated body 48, and is sized to provide an interference fit with the resilient aperture 28. A tool-engaging bore 60 extending from top flange 52 can also be provided. The tool-engaging bore 60 can comprise, for example, a hexagonal or threaded bore.

Figure 4B:
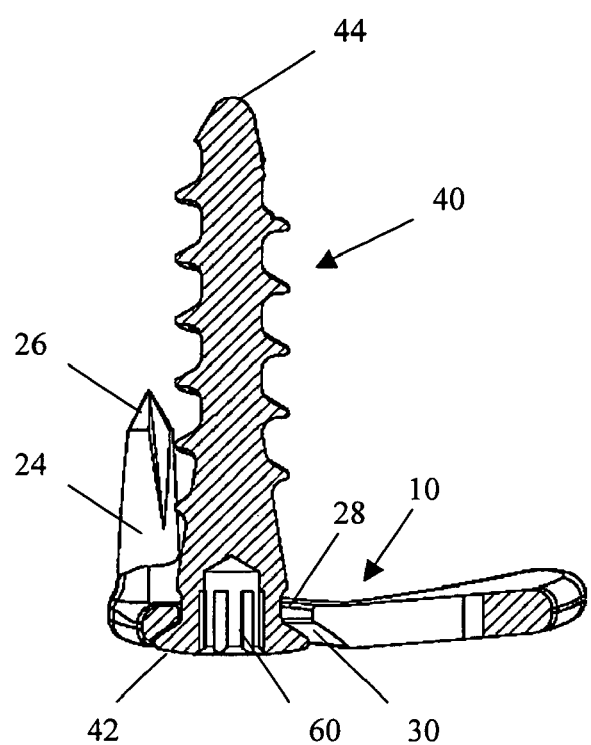
FIG. 4B is a cross-sectional view of the buttress staple and screw of FIG. 4A along lines A-A.

As further shown in FIGS. 4A and 4B, the head region 46 of the screw 40 is configured to be secured within the resilient aperture 28 of the screw locking plate 12. During assembly, the elongated body 48 expands the resilient aperture 28 as the screw 40 advances into the bone segment. Specifically, the contact band 56 adjacent to the last taper 58 is configured to be larger in width than the resilient aperture 28, thereby forcing the staple 10 to deform and the resilient aperture 28 to expand. Once the contact band 56 passes through the resilient aperture 28, the resilient aperture 28 is allowed to contract around the groove 54, thereby locking the screw 40 within the plate 12 itself. The contact band 56 is configured to have a diameter that is about 0.1 to about 0.2 mm larger than the width of the resilient aperture 28 to thereby form an interference fit therein. With the resilient aperture 28 having contracted back to its resting state, the screw 40 is locked from backing up during insertion. The groove 54 near the top flange 52 is configured to have a diameter that is smaller than the width of the resilient aperture 28 to provide the screw 40 with the ability to freely rotate after being locked in. Because of the ability of the screw locking plate 12 to lock in the screw 40, the staple 40 can also serve as a buttress staple 10 removal tool during revision surgery. For instance, when the screw 40 is being removed it is also lifting the buttress staple 10 at the same time since the screw 40 and the resilient aperture 28 have an interference fit.

It is contemplated that the components of the buttress staple and screw system 100 of the present invention can be formed from any biocompatible material, including metals such as titanium and titanium alloys. It is further contemplated that the buttress staple and screw system 100 of the present invention can be used with a variety of prostheses in a number of different applications. In fact, the present system 100 has applicability for any implant system where reinforcement of the implant may be desired.

It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. A buttress staple for preventing the migration of an implant, comprising:
    a screw locking plate including a first surface, a second, bone-contacting surface opposed to the first surface, and a resilient aperture having a depth extending from the first surface to the second surface, the resilient aperture in the form of a circle or oval having a predefined size in a normal, unexpanded condition, and being configured to expand and contract to receive a screw;
    a slit formed in a portion of the plate and extending through a perimeter of the resilient aperture the slit configured to allow the resilient aperture to expand and contract throughout the depth of the resilient aperture; and
    an anchoring post extending from the second, bone-contacting surface and configured for insertion into bone.

2. The staple of claim 1, wherein the slit terminates in a relief hole.

3. The staple of claim 2, wherein the relief hole is an aperture configured to receive a screw.

4. The staple of claim 1, wherein the resilient aperture includes a countersink on the first surface of the plate.

5. The staple of claim 1, wherein the anchoring post is tapered.

6. The staple of claim 1, wherein the anchoring post includes surface features for engagement with bone.

7. The staple of claim 6, wherein the surface features include sharp edges.

8. The staple of claim 7, wherein there are a plurality of anchoring posts.

9. The staple of claim 1, wherein the plate is bent with respect to a longitudinal axis thereof, and curved with respect to a transverse axis thereof.

10. The staple of claim 1, wherein the plate is defined by sidewalls connected by endwalls.

11. The staple of claim 10, wherein a midsection of each of the sidewalls extends towards a central region of the plate.

12. The staple of claim 10, wherein a midsection of each of the endwalls extends towards a central region of the plate.

13. The staple of claim 1, wherein the plate has a substantially bow tie-like shape.

14. A buttress staple and screw system for preventing the migration of an implant, comprising:
    a buttress staple including a first surface, a second, bone-contacting surface opposed to the first surface, a resilient aperture having a depth extending from the first surface to the second surface, the resilient aperture having a predefined shape and size, and being adapted to expand and contract to receive a screw the resilient aperture leading into a slit, the slit extending through the first and second surfaces, the slit configured to allow the resilient aperture to expand and contract throughout a depth of the resilient aperture, and an anchoring post extending from the second, bone-contacting surface and configured for insertion into bone; and
    a screw configured to be inserted into bone, the screw having a head region at a proximal end, the head region being configured to be secured within the resilient aperture, and an elongated body extending from the head region to a distal end of the screw, the elongated body including a threaded portion and a contact band extending around a circumference of the screw and being disposed proximal to a proximal-most thread, the contact band having a diameter that is greater than a diameter of the resilient aperture in a non-expanded condition.

15. The system of claim 14, wherein the slit terminates in a relief hole.

16. The system of claim 14, wherein the relief hole is an aperture configured to receive a screw.

17. The system of claim 14, wherein the predefined shape of the resilient aperture is selected from the group consisting of a circular hole and an oblong slot.

18. The system of claim 14, wherein the resilient aperture includes a countersink on the first surface of the buttress staple.

19. The system of claim 14, wherein the anchoring post is tapered.

20. The system of claim 14, wherein the anchoring post includes surface features for engagement with bone.

21. The system of claim 20, wherein the surface features include sharp edges.

22. The system of claim 21, wherein there are a plurality of anchoring posts.

23. The system of claim 14, wherein the plate is bent with respect to a longitudinal axis thereof, and curved with respect to a transverse axis thereof.

24. The system of claim 14, wherein the plate is defined by sidewalls connected by endwalls.

25. The system of claim 24, wherein a midsection of each of the sidewalls and endwalls extends towards a central region of the buttress staple.

26. The system of claim 14, wherein the head region of the screw includes a top flange and a groove extending about the circumference of the head region, with the contact band being disposed therebetween.

27. The system of claim 26, wherein the contact band provides an interference fit with the resilient aperture.

* * * * *